United States Patent
Hares

(10) Patent No.: US 11,209,954 B2
(45) Date of Patent: Dec. 28, 2021

(54) SURGICAL ROBOTIC SYSTEM USING DYNAMICALLY GENERATED ICONS TO REPRESENT ORIENTATIONS OF INSTRUMENTS

(71) Applicant: CMR SURGICAL LIMITED, Cambridge (GB)

(72) Inventor: Luke David Ronald Hares, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 120 days.

(21) Appl. No.: 16/060,489

(22) PCT Filed: Dec. 9, 2016

(86) PCT No.: PCT/GB2016/053884
§ 371 (c)(1),
(2) Date: Jun. 8, 2018

(87) PCT Pub. No.: WO2017/098259
PCT Pub. Date: Jun. 15, 2017

(65) Prior Publication Data
US 2018/0364891 A1 Dec. 20, 2018

(30) Foreign Application Priority Data

Dec. 11, 2015 (GB) .................................. 1521922
Aug. 31, 2016 (GB) .................................. 1614730

(51) Int. Cl.
*G06F 3/0481* (2013.01)
*A61B 34/00* (2016.01)
(Continued)

(52) U.S. Cl.
CPC .......... *G06F 3/04817* (2013.01); *A61B 34/25* (2016.02); *A61B 34/30* (2016.02);
(Continued)

(58) Field of Classification Search
CPC ... G06F 3/04817; G06F 3/0482; A61B 34/25; A61B 34/30; A61B 34/74;
(Continued)

(56) References Cited

U.S. PATENT DOCUMENTS 5,503,320 A * 4/1996 Webster ............... A61B 17/072
227/176.1
9,718,190 B2 * 8/2017 Larkin .................. A61B 1/0005
(Continued)

FOREIGN PATENT DOCUMENTS

| WO | 2005084570 A1 | 9/2005 | |
| WO | WO-2005084570 A1 * | 9/2005 | ............. A61B 34/20 |
| WO | 2011083374 A1 | 7/2011 | |

OTHER PUBLICATIONS

International Search Report and Written Opinion from corresponding PCT/GB2016/053884 dated Mar. 30, 2017.
(Continued)

*Primary Examiner* — Kavita Stanley
*Assistant Examiner* — Phoebe X Pan
(74) *Attorney, Agent, or Firm* — Lando & Anastasi, LLP

(57) ABSTRACT

A surgical robotic system comprising a processor configured to obtain a state signal associated with an instrument, obtain a state signal associated with an imaging device, determine an image pose position of the instrument in dependence on the obtained signals and determine an icon for display in dependence on the determined image pose position.

19 Claims, 5 Drawing Sheets

(51) Int. Cl.
*A61B 34/30* (2016.01)
*G06F 3/0482* (2013.01)
*A61B 34/20* (2016.01)
*A61B 90/98* (2016.01)
*A61B 90/00* (2016.01)
*A61B 90/92* (2016.01)

(52) U.S. Cl.
CPC ............ *A61B 34/74* (2016.02); *G06F 3/0482* (2013.01); *A61B 34/70* (2016.02); *A61B 90/08* (2016.02); *A61B 90/36* (2016.02); *A61B 90/92* (2016.02); *A61B 90/98* (2016.02); *A61B 2034/2055* (2016.02); *A61B 2034/2059* (2016.02); *A61B 2034/305* (2016.02); *A61B 2034/742* (2016.02)

(58) Field of Classification Search
CPC .... A61B 2034/2055; A61B 2034/2059; A61B 2034/305; A61B 34/70; A61B 2034/742; A61B 90/08; A61B 2090/08021; A61B 2090/0803; A61B 90/36; A61B 90/92; A61B 90/98
See application file for complete search history.

(56) References Cited

U.S. PATENT DOCUMENTS

| | | | | |
|---|---|---|---|---|
| 2003/0210812 A1* | 11/2003 | Khamene | ............... | A61B 90/36 382/128 |
| 2005/0182319 A1* | 8/2005 | Glossop | ................ | A61B 5/061 600/424 |
| 2007/0016174 A1 | 1/2007 | Millman et al. | | |
| 2007/0167722 A1* | 7/2007 | Bladen | .................... | A61B 5/06 600/407 |
| 2007/0225550 A1* | 9/2007 | Gattani | .................. | A61B 90/36 600/101 |
| 2008/0004603 A1* | 1/2008 | Larkin | ................... | B25J 9/1692 606/1 |
| 2008/0287771 A1* | 11/2008 | Anderson | ............. | A61B 5/055 600/410 |
| 2009/0088634 A1 | 4/2009 | Zhao et al. | | |
| 2009/0088773 A1* | 4/2009 | Zhao | .................... | G06K 9/3241 606/130 |
| 2009/0088897 A1 | 4/2009 | Zhao et al. | | |
| 2012/0316573 A1 | 12/2012 | Durant et al. | | |
| 2014/0081455 A1 | 3/2014 | Goldberg et al. | | |
| 2014/0114327 A1* | 4/2014 | Boudreaux | ........ | A61B 18/1445 606/130 |
| 2015/0012010 A1 | 1/2015 | Adler et al. | | |
| 2015/0031985 A1* | 1/2015 | Reddy | ................... | A61B 90/39 600/424 |
| 2015/0157411 A1 | 6/2015 | Choi | | |
| 2015/0173849 A1* | 6/2015 | Robinson | ............... | A61B 34/35 700/257 |
| 2015/0351864 A1* | 12/2015 | Kamon | .................. | A61B 34/25 606/130 |
| 2016/0151117 A1* | 6/2016 | Gibbs | ................ | A61B 17/1703 600/424 |
| 2016/0249984 A1* | 9/2016 | Janssen | ................ | A61B 6/5247 600/427 |
| 2016/0310218 A1* | 10/2016 | Ruckel | .................... | A61B 90/37 |
| 2017/0151027 A1* | 6/2017 | Walker | .................... | A61B 34/37 |
| 2017/0209232 A1* | 7/2017 | Larkin | ..................... | A61B 1/04 |
| 2017/0210012 A1* | 7/2017 | Larkin | ................... | A61B 34/37 |
| 2017/0305016 A1* | 10/2017 | Larkin | .................... | B25J 9/1692 |
| 2018/0078170 A1* | 3/2018 | Panescu | ............. | A61B 5/065 |
| 2018/0217734 A1* | 8/2018 | Koenig | ................ | G06T 7/0012 |
| 2019/0038349 A1* | 2/2019 | Koblish | ............... | A61B 5/6885 |
| 2019/0125455 A1* | 5/2019 | Shelton, IV | .......... | A61B 34/30 |
| 2020/0034969 A1* | 1/2020 | Isaacs | .................... | A61B 6/463 |
| 2020/0069373 A1* | 3/2020 | Yu | .......................... | A61B 5/066 |

OTHER PUBLICATIONS

United Kingdom Search Report from corresponding United Kingdom Application No. GB1614730.8 dated Feb. 22, 2017.

* cited by examiner

SURGICAL ROBOTIC SYSTEM USING DYNAMICALLY GENERATED ICONS TO REPRESENT ORIENTATIONS OF INSTRUMENTS

CROSS-REFERENCE TO RELATED APPLICATIONS

This application is a U.S. National Phase Application under 35 U.S.C. § 371 of International Application No. PCT/GB2016/053884, filed Dec. 9, 2016, which claims priority to United Kingdom Application No. 1521922.3, filed Dec. 11, 2015, and United Kingdom Application No. 1614730.8, filed Aug. 31, 2016, all of which are hereby incorporated by reference in their entireties for all purposes.

BACKGROUND

This invention relates to robotic systems, and to robotic systems comprising processors.

Robots are commonly used for a range of industrial tasks, and also for performing surgery. Robots can operate purely under programmatic control or they can be configured to respond to inputs in real time from a user interface. In the most complex and critical tasks, such as surgery, it is normal for a robot to operate under real-time command of an operator. To achieve this, the operator is presented with a suitable input device. This is typically a physical mechanism that can be moved by the operator in three dimensions. The control system of the robot senses the configuration of the input device. The control system is programmed to cause the robot arm/manipulator to move in response to the sensed configuration of the control mechanism. Additionally, it is normal for the robot to present to the user a visual indication of the state of the robot, to help the operator understand what inputs are required to achieve a certain task. The visual indication may be a video stream captured by a camera on or near the robot arm and presented to the operator on a display screen.

The robot can include a plurality of arms. Each arm can have an instrument at its distal end which can be operated by the operator to carry out desired tasks.

Where more than one arm is present, the robot can indicate to the operator which arm is being controlled. For instance, for two arms, the robot can indicate to the operator which arm is being controlled by the operator's left hand (i.e. by a left hand controller) and which arm is being controlled by the operator's right hand (i.e. by a right hand controller). One way of doing this is to cause the robot to show an image of the instrument being operated by the operator on the display. The image can be shown on the left or right of the display to indicate whether it is being controlled by the left or right hand (or left or right input device).

In some situations a plurality of instruments of the same type can be in use at the same time. In those situations it will not always be clear which of those instruments is being controlled by the operator at any given time. This can lead to the wrong arm and instrument being inadvertently moved by the operator, which can cause unnecessary disruption to the process being carried out by the operator. This is especially true in situations where the arms and instruments are being used in an enclosed space, such as at a surgical site, where unnecessary movements of the instruments can cause tissue damage.

There is a need for an improved robotic system.

SUMMARY

According to an aspect of the present invention there is provided a surgical robotic system comprising a processor configured to:
  obtain a state signal associated with an instrument;
  obtain a state signal associated with an imaging device;
  determine an image pose position of the instrument in dependence on the obtained signals;
  determine an icon for display in dependence on the determined image pose position; and
  output a display signal to cause a display device to display the icon.

Suitably the state signal associated with the instrument comprises at least one of a joint state signal associated with the instrument and an instrument state signal. Suitably the processor is configured to receive at least one of the joint state signal associated with the instrument and the instrument state signal; and/or determine at least one of the joint state signal associated with the instrument and the instrument state signal in dependence on one or more instrument control signal transmitted by the processor.

Suitably the state signal associated with the imaging device comprises at least one of a joint state signal associated with the imaging device and an imaging device state signal. Suitably the processor is configured to receive at least one of the joint state signal associated with the imaging device and the imaging device state signal; and/or determine at least one of the joint state signal associated with the imaging device and the imaging device state signal in dependence on one or more imaging device control signal transmitted by the processor.

Suitably at least one of the joint state signal associated with the instrument and the joint state signal associated with the imaging device comprises one or more of a position sensor signal and a torque sensor signal. Suitably at least one of the joint state signal associated with the instrument and the joint state signal associated with the imaging device comprises a position encoder signal.

Suitably the instrument state signal comprises a signal indicative of the arrangement of an end effector of the instrument.

Suitably the processor is configured to determine a pose position of the instrument in dependence on the state signal associated with the instrument; determine a pose position of the imaging device in dependence on the state signal associated with the imaging device; and determine the image pose position in dependence on the pose position of the instrument and the pose position of the imaging device.

Suitably the surgical robotic system comprises an instrument configured to output the instrument state signal. Suitably the surgical robotic system comprises a robot arm configured to output the joint state signal. Suitably the surgical robotic system comprises a display device for displaying the icon.

Suitably the processor is configured to determine a coordinate transform in dependence on the determined pose position of the instrument and the determined pose position of the imaging device.

Suitably the processor is configured to determine a change in the pose position of at least one of the instrument and the imaging device, and to determine an updated coordinate transform in dependence on the determined change.

Suitably the processor comprises a kinematics controller, and the kinematics controller is configured to determine an interface state in dependence on the state signals, the interface state comprising data associated with the icon for display.

Suitably the interface state comprises data permitting the rendering of the icon for display.

Suitably the surgical robotic system comprises a visual processor, the visual processor being configured to receive the interface state from the kinematics controller and to render the icon for display.

Suitably the kinematics controller is operable at a higher frequency than the visual processor.

Suitably the icon comprises a scale showing a rotational range of a joint, and the processor is configured to determine the rotational position of the joint and to cause the display on the scale of a marker indicative of the determined rotational position.

Suitably the processor is configured to indicate an active instrument by causing the corresponding icon to be highlighted in a list of icons.

According to another aspect of the present invention there is provided a method of determining an icon for display in a robotic surgical system, the method comprising:
 obtaining a state signal associated with an instrument;
 obtaining a state signal associated with an imaging device;
 determining an image pose position of the instrument in dependence on the obtained signals;
 determining an icon for display in dependence on the determined image pose position; and
 outputting a display signal to cause a display device to display the icon.

Any one or more feature of any aspect above may be combined with any one or more feature of any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF DRAWINGS

The present invention will now be described by way of example only with reference to the accompanying drawings. In the drawings.

DETAILED DESCRIPTION

The following description describes the present techniques in the context of robotic surgical systems, though the features described below are not limited to such systems, but are applicable to robotic systems more generally.

Robotic systems can include manufacturing systems, such as vehicle manufacturing systems, parts handling systems, laboratory systems, and manipulators such as for hazardous materials or surgical manipulators.

Figure 1:
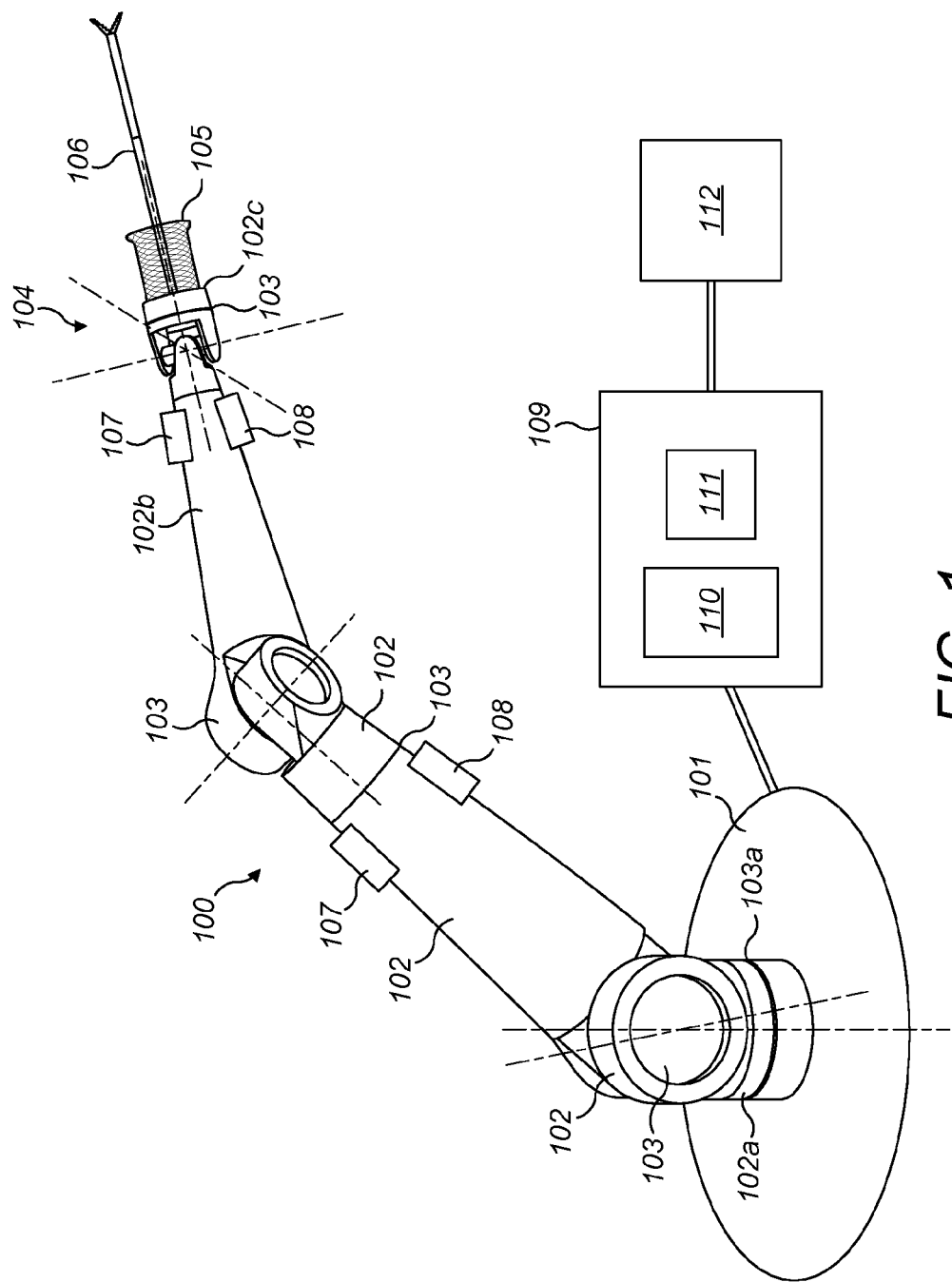
FIG. 1 illustrates a surgical robot arm.

FIG. 1 illustrates a surgical robot having an arm 100 which extends from a base 101. The arm comprises a number of rigid limbs 102. The limbs are coupled by revolute joints 103. The most proximal limb 102a is coupled to the base by a proximal joint 103a. It and the other limbs are coupled in series by further ones of the joints 103. Suitably, a wrist 104 is made up of four individual revolute joints. The wrist 104 couples one limb (102b) to the most distal limb (102c) of the arm. The most distal limb 102c carries an attachment 105 for a surgical instrument 106. Each joint 103 of the arm has one or more motors 107 which can be operated to cause rotational motion at the respective joint, and one or more position and/or torque sensors 108 which provide information regarding the current configuration and/or load at that joint. Suitably, the motors are arranged proximally of the joints whose motion they drive, so as to improve weight distribution. For clarity, only some of the motors and sensors are shown in FIG. 1. The arm may be generally as described in our co-pending patent application PCT/GB2014/053523.

Figure 2:
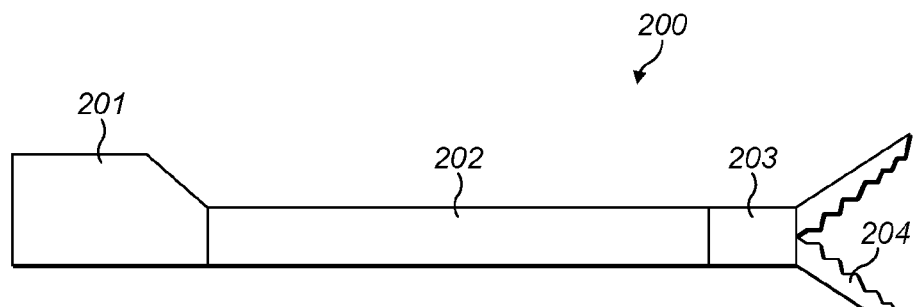
FIG. 2 illustrates an instrument for use with the arm of FIG. 1.

The arm terminates in the attachment 105 for interfacing with the instrument 106. Suitably, the instrument 106 takes the form described with respect to FIG. 2. FIG. 2 illustrates a typical surgical instrument 200 for performing robotic laparoscopic surgery. The surgical instrument comprises a base 201 by means of which the surgical instrument connects to the robot arm. A shaft 202 extends between the base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 105 comprises a drive assembly for driving articulation of the instrument.

The instrument 106 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument.

Controllers for the motors, torque sensors and encoders are distributed within the robot arm. The controllers are connected via a communication bus to a control unit 109. The control unit 109 comprises a processor 110 and a memory 111. The memory 111 stores in a non-transient way software that is executable by the processor to control the operation of the motors 107 to cause the arm 100 to operate. In particular, the software can control the processor 110 to cause the motors (for example via distributed controllers) to drive in dependence on inputs from the sensors 108 and from a surgeon command interface 112. The control unit 109 is coupled to the motors 107 for driving them in accordance with outputs generated by execution of the software. The control unit 109 is coupled to the sensors 108 for receiving sensed input from the sensors, and to the command interface 112 for receiving input from it. The respective couplings may, for example, each be electrical or optical cables, or may be provided by a wireless connection. The command interface 112 comprises one or more input devices whereby a user can request motion of the end effector in a desired way. The input devices, or input controllers, could, for example, be manually operable mechanical input devices such as control handles or joysticks, or contactless input devices such as optical gesture sensors. Commands input by the input devices can include movement commands, for example to move the instrument in a particular way, such as a lateral movement and/or a rotation. Such commands can include end effector commands, for example to control an end effector coupled to a distal end of the instrument to operate the end effector, such as to open/close gripper jaws or to operate (turn on or off) an electrosurgical end effector.

Suitably a user console, such as a surgeon console, comprises two input devices.

The input device may be associated with one of a left hand control and a right hand control. Suitably, where there are a plurality of input devices, one of the input devices is associated with a left hand control and another of the input devices is associated with a right hand control.

In other words, one of the input devices may be configured to be operated by a user's right hand (a right hand control, which is suitably provided towards the right hand side of the user console) and another of the input devices may be configured to be operated by a user's left hand (a left hand control, which is suitably provided towards the left hand side of the user console).

The software stored in the memory 111 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the command interface 112 can control the instrument 106 to move in such a way as to perform a desired surgical procedure. The control unit 109 and/or the command interface 112 may be remote from the arm 100.

Figure 3:
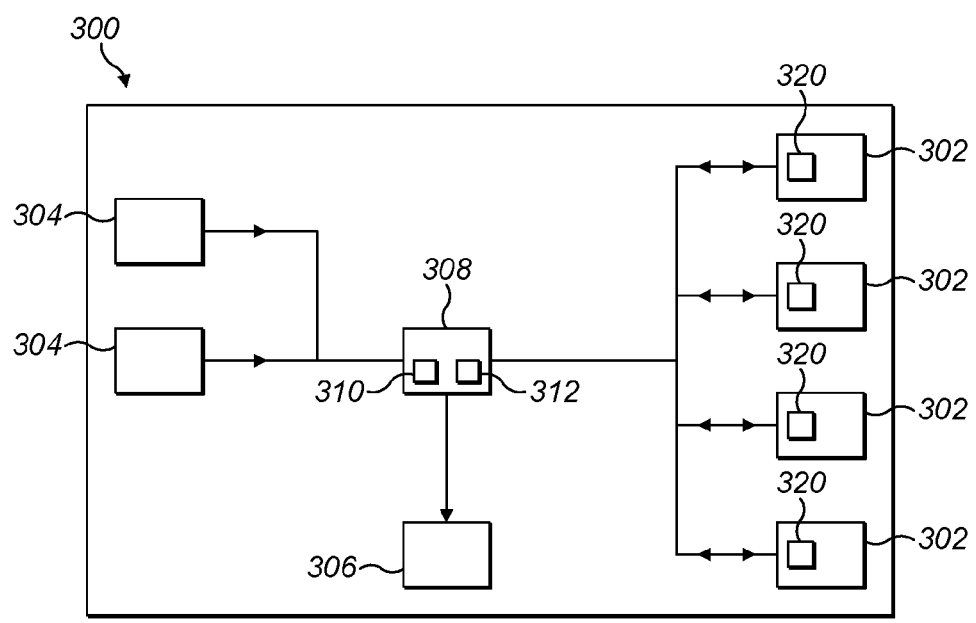
FIG. 3 illustrates a schematic of a robotic surgical system.

A schematic of a robotic surgical system will now be described with reference to FIG. 3. A robotic surgical system 300 comprises a plurality of robot arms 302, a plurality of (usually two) input devices 304, a display device 306 such as a screen and a central processor 308. The central processor 308 may comprise a plurality of processors. The central processor suitably comprises a kinematics controller 310 and a visual processor 312. The robot arms 302 are provided with surgical instruments, and/or other implements, 320 such as grippers, cutters, cauterisers, needles, imaging devices (for example a camera such as an endoscope), or the like, at their distal ends. The robot arms 302, input devices 304 and the screen 306 are operatively connected to the central processor 308. The central processor 308 is responsive to signals received from the input devices 304, the robot arms 302 and the instruments 320, and can provide signals to the robot arms 302, the instruments 320 and the screen 306. The central processor 308 receives the signals from the input devices 304 and processes the signals so as to output drive signals for driving one or more of the robot arms 302 and/or one or more of the instruments 320. The drive signals are sent by the central processor to the respective robot arms 302 and instruments 320.

Suitably the imaging device is configured to output an image signal. Suitably the image signal comprises an image. The image signal suitably comprises a video signal.

Whilst the above description refers to a single screen as a display device, in some examples the robotic surgical system comprises a plurality of display devices, or screens. The screens are suitably configured to display the image as a two-dimensional image and/or as a three-dimensional image. The screens can be provided on a single user console, or two or more consoles can comprise at least one screen each. This permits additional viewing screens which can be useful for allowing people other than the console user to view the surgical site, for example for training.

A user can control the robot arms 302 and the instruments 320 coupled to the robot arms 302 via the input devices 304 and can manipulate the robot arms and/or the instruments as desired. Manipulation of the instruments 320 includes manipulation or operation of the end effector of the instrument. In other words, opening or closing jaws of an end effector, or activating or deactivating an electrosurgical tool such as a cauteriser.

Suitably the robot arms 302 and/or instruments 320 are configured to send signals to the central processor 308. In some examples, these signals comprise position and/or orientation signals indicative of the respective robot arm 302 or instrument 320 position and/or orientation.

In the foregoing, the robotic system may be configured to send and receive signals by wired connections. Suitably the robotic system comprises one or more wireless transceivers to wirelessly transmit and/or receive signals. This permits a reduction in the need for wired connections through the robotic system. Suitably the robotic system is configured to send and/or receive signals by wireless and/or wired signals.

Suitably at least one of the input devices 304 and the robot arms 302 comprise a first wireless transmitter, a first wireless receiver and/or a first wireless transceiver. Suitably the central processor comprises a second wireless transmitter, a second wireless receiver and/or a second wireless transceiver for communicating with the respective one of the first wireless receiver, first wireless transmitter and/or first wireless transceiver.

Suitably the instrument 320 comprises the respective one of the first wireless transmitter, first wireless receiver and/or first wireless transceiver.

Figure 4:
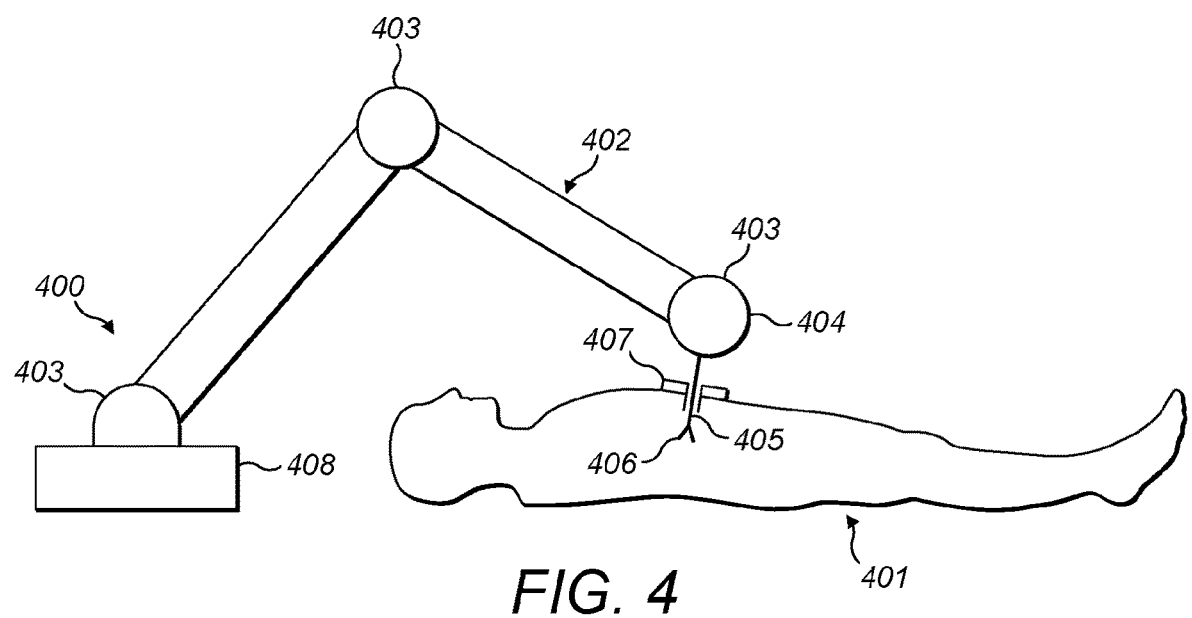
FIG. 4 illustrates a surgical robot.

The user may be remote from the arms 302 and the instruments 320, and so may not be able to see them directly. The instruments 320 may be embedded within a surgical site, preventing direct observation. An example of such a set-up is illustrated in FIG. 4. FIG. 4 illustrates a typical surgical robot 400 which consists of a base 408, an arm 402, and an instrument 405. The base supports the robot, and is itself attached rigidly to, for example, the operating theatre floor, the operating theatre ceiling or a trolley. The arm extends between the base and the instrument. The arm is articulated by means of multiple flexible joints 403 along its length, which are used to locate the surgical instrument in a desired location relative to the patient. The surgical instrument is attached to the distal end 404 of the robot arm. The surgical instrument penetrates the body of the patient 401 at a port 407 so as to access the surgical site. At its distal end, the instrument comprises an end effector 406 for engaging in a medical procedure.

Whilst FIG. 4 illustrates a single arm with a single instrument, in practice multiple arms and instruments will be used. One arm is coupled to an imaging device which provides image signals representative of the surgical site. For example, the imaging device can be an endoscope. The endoscope can provide an image feed, such as a video stream, from the surgical site.

The image provided by the imaging device enables the user to see the end effectors at the surgical site. This enables the user or operator of the robotic surgical system 300, such as a surgeon, to effect control over the instruments to effect surgery.

In many surgical procedures it is desirable for the user to be able to select from among two or more instruments 320. For example, an input device 304 is usable to control a plurality of instruments 320. The input device 304 is usable to control one instrument when coupled to the one instrument, and is usable to control another instrument when coupled to that other instrument. In other words, an input device 304 is usable to control the instrument 320 to which it is operatively coupled. The coupling between input device and instrument is changeable. One instrument can be controlled by a plurality of input devices. The instrument is coupleable to one input device to permit control of the instrument by the one input device. Once decoupled from the one input device, the instrument is coupleable to another input device to permit control of the instrument by that other input device. Thus more than one instrument 320 can be operatively associated with a single input device 304.

The input device 304 is associatable with, or operatively coupleable to, one instrument 320 at a time. This association or coupling is, in one example, effected in software control. The user selects the desired coupling, for example by manipulating the respective input device 304 to select the respective instrument 320, such as using a button or joystick control to select an option from a menu in an interface. The input device itself need not be used to make this selection. Another button or control, such as a foot pedal or switch on the user console, can be used instead of or as well as the input device. This provides flexibility in the selection of the instrument. The instrument that is operatively coupled to an input device can be termed an active instrument. Instruments that are not operatively coupled to an input device can be termed non-active instruments. This means that they are not, at that time, being actively controlled by an input device. Suitably the processor is configured to determine which of the instruments is the active instrument.

The robotic system is suitably configured to determine a mapping between the input device and the robot arm and/or instrument. Suitably the mapping is such as to ensure that where an input device detects motion of a user in one direction, the instrument is driven in a corresponding direction. For example, motion of a user to the left can cause the instrument to be driven to the left. Where the image displayed on the display device is a mirror image (about a vertical axis) of the image captured by the imaging device, motion of a user to the left can cause the instrument to be driven to the right (which will appear as being driven to the left on the display device). This mapping suitably enables natural control of the robot arms/instrument by motion of the user. The mapping suitably changes in dependence on how the image is processed before being displayed, for example, rotated and/or mirrored.

The robotic system may be configured to determine the mapping in dependence on at least one of the position and orientation of the imaging device and at least one of the position and orientation of the instrument.

Suitably the robotic system is configured to update the mapping on movement of the imaging device (which will alter the apparent positions of the instrument in the image as displayed on the display device).

In a situation where there are three instruments 320 (for example a cauteriser, a gripper and a needle) associatable with an input device 304, the active instrument can be identified to the user via an interface, such as an interface on or displayed on the display device 306. Suitably the display device 306 is configured to display an image captured by the imaging device. The captured image can be overlaid by graphics which represent active, and optionally also non-active, instruments coupled to, or coupleable to, one or more input devices. The captured image and the overlaid graphics together comprise a displayed image. Advantageously the displayed image permits an intuitive understanding of which instruments are active instruments. For example, the display device 306 can be configured to display a representation of the instrument, or preferably the end effector of the instrument. Where a gripper is the active instrument, i.e. is being controlled, the display device can show a displayed image comprising a representation such as an icon of a gripper end effector in, for example, the top right hand corner of the displayed image. This lets the user know that the gripper is the active instrument even when the gripper is not being moved. In general, the icon suitably corresponds to the instrument. The icon provides a visual indication permitting matching of the icon to the instrument.

It is further desirable for the user to easily identify which instrument 320 is currently operatively associated with an input device 304 (i.e. which instrument is active, or is being controlled) at any one time even where more than one type of instrument 320, and/or more than one of any one type of instrument, is present. In a situation where there is more than one of a given type of instrument 320, say more than one gripper, then a displayed image comprising a representation of a gripper may not allow unambiguous identification of which of the gripper instruments is the one that is active. Identification of the active instrument can be achieved by causing the displayed image to display a representation of the instrument 320, such as an icon, in an orientation that matches that of the end effector or instrument itself. For example, the orientation of the representation of the instrument (or icon) in the displayed image can match the orientation of the end effector in the frame of the captured image that is displayed as part of the displayed image.

Suitably the representation of the instrument end effector comprises at least one of an image, a pictogram and an ideogram. Suitably the processor is configured to cause the representation of the instrument end effector to comprise at least one of an image, a pictogram and an ideogram. The representation of the instrument end effector can be two-dimensional or three-dimensional.

The orientation, and in some examples also the position, of the end effector of an instrument can be termed the pose position of that end effector or instrument. The pose position is suitably used in determining the representation of the instrument for display in the displayed image. In other words, as part of causing the display device to display the displayed image, the pose position of the end effector can be determined, and based on that determination, the representation of the end effector to be displayed on the display device can be determined.

The pose position of an instrument can be determined with respect to any desired frame of reference. It is convenient to determine the pose position of an instrument with respect to the frame of reference of the base of the robot arm to which the instrument is coupled. This is because the robot arm comprises the one or more position and/or torque sensors 108 described above. These sensors provide information regarding the current configuration of the arm. Thus, knowledge of the outputs from these sensors permits a determination of how each limb of the arm is arranged relative to a proximal limb, and so the arrangement (i.e. orientation and optionally also position) of the instrument can be determined relative to the base of the robot arm.

For displaying as part of the displayed image, it is desirable that the pose position of the instrument in the frame of reference of the imaging device (i.e. as viewed by the imaging device) is known. This is to ensure that the orientation of the icon matches that of the instrument as viewed in the image.

The pose position of the instrument in the frame of reference of the image can be termed the image pose position. The image pose position can be determined from the pose position by a coordinate transform. The determination of the pose position, and the coordinate transform, will be explained in more detail below.

The pose position can be determined in a number of ways. In a first example, the pose position of the instrument is determined in dependence on signals output from the position and/or torque sensors 108. Each sensor will output a signal representative of the position and/or torque of the joint associated with that sensor. In other words, a first position and/or torque sensor which is configured to sense the position of a first joint and/or sense torque about the first joint will output one or more signal in dependence on the position of the first joint and/or torque about the first joint. The position and/or torque sensors comprise, in one example, a position encoder configured to determine the position of the joint.

The one or more signal output by the position and/or torque sensor can be a joint state signal for the respective joint. Each position and/or torque sensor is configured to transmit the output signal(s) (i.e. the joint state signal) to the central processor. The central processor is configured to obtain or acquire, for example by receiving, from each position and/or torque senor, the output signals (i.e. the joint state signals).

The instrument is configured to output an instrument state signal in dependence on the state of the instrument. The state of the instrument comprises the arrangement of the end effector (where the end effector is movable). In other words, where the end effector is a gripper, the state of the instrument comprises the state of the gripper: whether it is open, closed, or in some intermediate configuration. For example, the state of the instrument comprises the angle of separation of the jaws of the gripper. Suitably where the end effector comprises separate elements, such as jaws, the separate elements are separately controllable. For example each of a pair of jaws are independently controllable. Suitably the state of the instrument comprises a state of each of the separate elements, or jaws. Where the end effector comprises an electrosurgical tool, the state of the instrument comprises the activation state of the electrosurgical tool, for example whether the tool is electrically activated, not electrically activated, and/or other related information such as the temperature of the tool (noting that after electrical activation, the temperature of the tool will remain elevated for a given period of time).

Suitably the instrument comprises one or more sensor to determine at least a portion of the state of the instrument. The instrument is configured to transmit the instrument state signal to the central processor. The central processor is configured to obtain or receive, from the instrument, the instrument state signal.

The central processor is configured to determine the position and/or orientation of the instrument, or of the end effector of the instrument, in dependence on the received joint state signals and the received instrument state signal. The central processor is configured to determine the pose position of the instrument in dependence on the received joint state signals and the received instrument state signal.

In addition to receiving joint state signals and instrument state signals from arms coupled to instruments for carrying out surgery, the central processor is configured to receive joint state signals and an instrument state signal from the robot arm coupled to the imaging device. In this instance, the instrument state signal can comprise information associated with the imaging device, such as its field of view and/or gaze axis, i.e. the axis along which the imaging device is oriented, or what the centre of the view is pointing at. The pose position of the imaging device can be used to determine the coordinate transform necessary to transform the pose position of the instrument to the image pose position.

The central processor is configured to determine the pose position of the instrument, the instrument to be represented in the displayed image, and the pose position of the imaging device. The pose position of the instrument and the pose position of the imaging device are suitably determined in the same frame of reference. For example, each of the robot arms will be mounted to a known location in the operating theatre. Hence the spatial positioning and orientation of the base of each robot arm will be known (or can be determined by the central processor). Thus the pose position of the instrument and of the imaging device can be determined in the frame of reference of the operating theatre.

In dependence on knowledge of the pose position of the instrument and of the pose position of the imaging device, the central processor is configured to determine the coordinate transform required to transform the pose position of the instrument in the frame of reference of the operating theatre (or some other selected frame of reference) to the image pose position, i.e. the pose position of the instrument in the frame of reference of the imaging device. This coordinate transform from one frame of reference to another can be achieved in any convenient way.

In other words, in dependence on knowledge of the position and orientation of the imaging device, and the position and orientation of the other instruments, the central processor is enabled to determine the pose position of the other instruments in the frame of reference of the imaging device, i.e. how these other instruments will appear as viewed from the imaging device. Thus the image pose position is determinable by the central processor. The central processor is configured to determine the image pose position in dependence on the pose position and the determined coordinate transform.

The instrument is movable in response to commands sent from the user console, for example commands generated in dependence on movements of the input device coupled to the instrument. Movement of the instrument will cause the pose position of the instrument to change. The central processor is configured to update the coordinate transform in dependence on determining a change in the pose position of the instrument. Thus, as the instrument is moved, the determined image pose position can be updated to reflect the changes in the instrument's position and/or orientation relative to the imaging device. In a preferred implementation, the central processor is operable in a continuous fashion.

Operating in a continuous fashion comprises operating without a delay between subsequent operations. This may be in contrast to a periodic operation, where an operation occurs once every given time period. The central processor is configured to continuously calculate the coordinate transform. The central processor is configured to continuously determine the pose position of the instrument and/or the pose position of the imaging device. Suitably, the central processor is configured to continuously update the coordinate transform.

The imaging device is also movable in response to commands sent from the user console. Movement of the imaging device will change the coordinate transform. The central processor is suitably configured to determine a movement of the imaging device (for example a change in the pose position of the imaging device), and to update the coordinate transform in dependence on determining a change in the pose position of the imaging device. Thus, as the imaging device is moved, the determined image pose position of an instrument can be updated to reflect the changes in the instrument's position and/or orientation relative to the imaging device.

Similarly, both the instrument and the imaging device may move. The central processor is configured to determine a change in both the pose position of the instrument and the pose position of the imaging device, and to determine an updated coordinate transform as appropriate in dependence on the new pose positions.

The joint state signals can comprise signals in arbitrary units. In this case, the central processor is configured to convert the arbitrary units to 'proper' or 'real world' units, such as angle of orientation in degrees, or position in three-dimensional space in metres. Other units can be used as appropriate.

At least one of the joint state signal and the instrument state signal need not be transmitted to the central processor from the arm or instrument, respectively. Additionally or alternatively, the joint state signal and/or the instrument state signal can be obtained or acquired, for example by being determined by the central processor, in dependence on one or more control signal sent by the central processor to the arm and/or instrument. Where the central processor transmits a control signal to the instrument, the central processor has knowledge of the desired state of the instrument. In other words, where the central processor transmits a control signal to the instrument to open both jaws of a gripper fully, the central processor will be able to determine that the jaws of that instrument are in the fully open position without necessarily needing to receive a signal from the instrument to that effect. The central processor may be configured to determine any associated delay in the actuation of the instrument in response to the transmitted control signal, and to take this into account in the determination of the instrument state signal. Similarly, the joint state signal can be determined by the central processor in dependence on the control signals transmitted to each joint. The one or more control signal may comprise the desired position, orientation and/or operation state of the arm (or each joint) and/or the instrument.

In a preferred implementation, the central processor is configured to receive a joint state signal associated with the instrument, and to determine the instrument state signal in dependence on one or more control signal transmitted to the instrument.

In another example, the pose position of the instrument, or the pose position of the imaging device, can be obtained or acquired, for example by being determined by the central processor, in dependence on knowledge of a previous state of the robot arm to which the instrument is coupled and of the instrument, or of the robot arm to which the imaging device is coupled and of the imaging device, and knowledge of drive signals sent to the respective arm, instrument and/or imaging device to drive one or more joints of the respective arm to a new configuration and/or to drive the instrument and/or imaging device to a new configuration.

For example, the input device can be used to input a control to move the instrument to a new location. The input device can be used to input a control to alter the state of the instrument, such as opening the jaws of a gripper. In dependence on the input device inputting such control commands, the central processor can determine one or more drive signals to send to the arm and/or instrument to effect control of the arm and/or instrument as desired. The central processor is suitably configured to determine a desired movement of the arm and/or a desired change in the state of the instrument in dependence on received input commands and to determine one or more drive signal to effect control of the arm and/or instrument as desired. The central processor is suitably configured to send the one or more drive signal to the arm and/or instrument. The arm and/or instrument is configured to receive the one or more drive signal and to effect movement so as to achieve the desired movement.

A previous state of the instrument can be determined on the basis of joint state signals and instrument state signals received by the central processor prior to the central processor outputting the one or more drive signal, and/or on the basis of one or more control signal transmitted by the central processor. As described above, the central processor can determine the position and/or orientation of the arm and configuration of the instrument in dependence on the received joint state signals and instrument state signals. The central processor is suitably configured to determine the previous state of the instrument in real time. Alternatively, the central processor is configured to determine the previous state of the instrument at one or more stages in a processing cycle, and to store the determined previous state of the instrument in memory, for example in a look-up table. The stage or stages in the processing cycle can suitably be each clock cycle, or a multiple of clock cycles such as a predetermined multiple (for example determined in dependence on the refresh rate of the display device, or an update rate of the display), and/or immediately following a movement of the arm and/or instrument.

The central processor is suitably configured to determine an updated state of the instrument in dependence on the previous state of the instrument and the drive signal(s) sent to the instrument. For example, if the previous state of the instrument comprises a determination that a gripper instrument is in position (x, y, z), orientation $\alpha°$ and the jaws are closed, and drive signals are sent to move the instrument 2 units in the positive x-direction and 3 units in the negative z-direction, to change the orientation by 10° in a positive sense and to fully open the jaws, then the central processor can determine that the updated state of the instrument is in position (x+2, y, z−3), orientation ($\alpha+10°$) and that the jaws are fully open. The (x, y, z) origin, orientation and units can be determined as desired. Similarly the orientation can be determined as desired, and the positive and negative orientations chosen to represent a rotation to either side of a desired orientation.

In another example, the pose position of an instrument can be determined by visual targeting. For example visual targeting can be used for position determination. In this example, visual targets (beacons or reference indicators) are located at known locations on the robot arms and on the instrument (suitably on a portion of the instrument that is visible from outside the patient, such as a proximal portion of the instrument). A camera (or cameras, suitably spaced from each other around the room) are used to track the position of the arms and instruments by using those visual targets. This approach can be useful in cases where an arm might be 'floppy' (i.e. where it doesn't necessarily remain located precisely as driven, but may instead permit some play or tolerance in the location) or where there isn't enough trust in the output from the sensors such as the position encoders.

Providing a visual target on a portion of the instrument visible from outside the patient permits the position of the instrument to be tracked by a camera external to the patient. This can avoid the need to track a visual target on a portion of the instrument located within the patient using the imaging device, the image from which might be obscured by tissue or fluids. Alternatively or additionally, a visual target is suitably provided on a portion of the instrument locatable within the patient during a surgical procedure, and which is trackable by the imaging device.

Suitably the processor is configured to analyse the image signal and detect the visual targets in the image represented by the image signal. The visual targeting can use at least one of image analysis, edge analysis and other suitable image processing techniques to determine the location of the visual targets within the field of view of the tracking cameras, and hence the position and/or orientation of the instrument in the frame of reference of, for example, the operating theatre or the image.

Hence the pose position of the instrument can be determined. In this way, a system similar to that described above can be used, but with the pose position being determined from image-derived position and/or orientation data rather than from joint signal-derived position and/or orientation data.

Where the pose position of the instrument is determined from the image captured by the imaging device, this might lead directly to an image pose position. In other words, the determined pose position of the instrument determined from an image captured by the imaging device will already be in the frame of reference of the imaging device. In this case, there will be no need for the coordinate transform, and so this step can be omitted.

A combination of one or more of the above-described methods of determining the pose position and/or of determining the image pose position of an instrument can be used. This might be used as a check, in cases where accurate determination of pose positions and/or of image pose positions is desired.

As described above, the central processor can determine the image pose position of an instrument. The state of an icon (i.e. a representation of the instrument) is calculated based on the determined image pose position. In some examples, the state of the icon can be calculated in dependence on orientation information in the image pose position. In other words, knowledge of the position information is not necessary.

Knowledge of the status of each individual joint is not necessary, as long as the resulting orientation of the instrument in the image pose position is determinable. Thus, the central processor can be configured to determine the orientation of the instrument in the image pose position based on a subset of the data needed to determine the full position and orientation of the instrument.

The central processor 308 comprises a kinematics controller 310. The kinematics controller 310 is suitably configured to receive the signals such as the joint state signals and instrument state signals. The kinematics controller is configured to analyse the received signals and to output data permitting the rendering of the icon.

Suitably the kinematics controller 310 is configured to process telemetry data to render the icon. In other words, the telemetry data is processed as normal by the central processor 308. This ensures that processing associated with rendering the icons does not affect data relied on by any other portion of the system. Suitably, the output of processing carried out for the purposes of rendering the icons is used just to render the icons. Suitably nothing else depends on the icon data. Thus data that is critical to the operation of the robotic system is not affected by the icon processing or rendering. The icon rendering or processing can be carried out downstream of the standard data processing. This permits maintaining safety of operation.

In some examples, the robotic system may comprise an icon library. The robotic system suitably comprises a memory. The memory suitably comprises the icon library. The icon library suitably comprises a plurality of icons of different types, orientations and or poses. For example, the icon library may comprise icons relating to at least one instrument for use with the robotic system, the icons associated with a particular instrument corresponding to a series of views of the instrument (or at least of the end effector of the instrument) at different orientations or angles. For example, showing the complete range of possible orientations at a predetermined angular interval. The angular interval may be 5 degrees, 2 degrees, 1 degree, or any other suitable angle. The icons need not exactly match the determined pose position of the instrument. The closest-matching icon from the library can be selected. Suitably this permits identification of the instrument to which the icon relates. Thus, in these examples, the visual processor may be configured, as part of rendering the icon or generating the interface for display, to select the icon closest to the determined pose position.

In a preferred example, the interface for display on the display device 306 is generated by a visual processor 312. The visual processor is suitably configured to render the icon for display. The visual processor is suitably separate from the kinematics controller 310. Referring to FIG. 3, the central processor 308 comprises the visual processor. Alternatively the visual processor can be separate from the central processor. The visual processor can therefore be concerned only with image output. I.e. no critical system in the robotic system depends on the output of the visual processor.

As mentioned above, the central processor may be operable in a continuous fashion. The visual processor is suitably operable in a continuous fashion. The visual processor is suitably configured to generate the interface for display in a continuous fashion. Thus the kinematics controller can be configured to continuously output data, and the interface can be continuously generated in dependence on the data output by the kinematics controller. In some examples, the visual processor need not operate continuously. It may be sufficient for the visual processor to operate at the frame rate at which the interface generated by the visual processor is to be displayed.

The visual processor 312 need not operate at the same frequency as the central processor 308 and/or the kinematics controller 310. The visual processor can be configured to operate at a lower frequency than the central processor and/or the kinematics controller. The frequency at which the visual processor is configured to operate suitably depends on the desired frame refresh rate of the displayed image. Suitably the frequency at which the visual processor is configured to operate is equal to or greater than the desired frame refresh rate.

The central processor and/or kinematics controller may be required to operate at a relatively higher frequency (which might be in the order of several hundreds of Hertz) so as to satisfy safety requirements. The frame refresh rate of the displayed image is likely to be much lower than this, and in one example is of the order of 120 Hertz, or 60 Hertz. Operating the visual processor at a slower operating frequency can be more efficient in terms of processing. This can mean that a slower processor can be used as the visual processor. Suitably the frequency of operation of the visual processor 312 and/or the frame refresh rate of the displayed image is higher than a human perception limit, so that the icon rendering and changes appear smooth.

As mentioned above, the kinematics controller is configured to perform the analysis and calculations on the input data and to output data on which the icon rendering can be based. That is to say, the kinematics controller outputs data corresponding to what should be displayed on the display device as part of the displayed image. The kinematics controller is suitably configured to output the image pose position information, data relating to the type of instrument and/or where the icon is to be displayed on the display device. The kinematics controller thus handles the interface state. The interface state comprises information necessary to render the display, including the icon. The visual processor is configured to perform the necessary processing of the information output by the kinematics controller so as to generate the displayed image. The visual processor performs the processing and rendering to generate the interface according to the interface state output by the kinematics controller. This can relieve the burden on the kinematics controller by shifting the image processing to the visual processor. The output from the kinematics controller need not be calculated specifically for the purpose of generating the icon and/or interface. Suitably the visual processor is configured to generate the interface in dependence on data output by the kinematics controller in the course of its normal operations (i.e. without carrying out additional operations relating to and/or exclusively for the purpose of rendering the interface).

In the example discussed above, the kinematics controller outputs data relating to the image pose position. In other words, the kinematics controller performs the coordinate transform. In an alternative example, the kinematics controller is configured to output data relating to the pose positions of the respective instruments (including the imaging device) and the visual processor is configured to perform the coordinate transform.

The image pose position is used to render the icons. Icons are rendered from the point of view of an imaginary 'icon camera'. I.e. the rendering of the icons does not necessarily directly relate to the instrument as viewed in the displayed image. Suitably, the distance between the notional icon camera and the icon does not change in response to a variation in distance between the instrument and the imaging device. In other words, the magnification of the icon on the interface does not change. Thus as an instrument is moved closer to or further away from the imaging device, the icon representation corresponding to that instrument will not change in size. The rendering of the icon is suitably based on a three-dimensional model. The size of this three-dimensional model does not change.

The visual processor is configured to render the icon such that the icon is consistently placed within the centre of an icon area. The visual processor is suitably configured to render the icon for each frame, i.e. a new render is performed for each frame of the displayed image. As an instrument rotates and/or moves (for example about one or more of a pitch axis, a yaw axis, a roll axis, and/or the end effector operates such as by opening or closing at least partially), the icon render is re-framed so as to fit within the centre of the icon area.

It is important that the icon is visible when rendered in the icon area. In other words, the icon should not be a small dot within the icon area, and nor should the icon be so large that only a portion of the icon is visible within the icon area. Suitably the visual processor is configured to render the icon such that it optimises or maximises use of the space within the boundary of the icon area. Suitably the visual processor is configured to render the icon so that there is no change in magnification between an icon that represents an instrument that is viewed straight-on and, for example, with jaws open, and an icon that represents an instrument that is viewed curled up and, for example, with jaws closed. In other examples, the visual processor is configured to change the magnification of the icon in response to orientation and/or operation of the end effector. For example, if the orientation of the end effector changes and/or the end effector operation changes (such as by the opening of jaws), the magnification of the icon can be changed to ensure that the icon remains within the icon area. This approach can permit the re-sizing of the icon to optimise or maximise use of space in the icon area.

In one example, there may be difficulty in identifying the instrument from an icon when the end effector aligns along the axis of the imaging device. The angle of the instrument may make the corresponding rendered icon indistinguishable from that of another instrument, or may make the corresponding rendered icon unidentifiable. In this case the visual processor is suitably configured to change the projection of the icon to permit the instrument corresponding to that icon to be distinguished and/or identified. The projection of the icon can be changed from being along the axis of the imaging device (as in a standard configuration) to being a projection which is not along the axis of the imaging device. In one example the render of the icon is three-dimensional when the projection is along the axis of the imaging device, and two-dimensional when another projection is used in the render. This permits a user to readily distinguish when another projection is used.

The visual processor is suitably configured to take account of information other than the orientation of the instrument when generating the icon. Such information can include, for example, the lifetime, or lifetime remaining, of the instrument and/or the usage history of the instrument. Suitably the visual processor is configured to take account of the state of the instrument, including the state of operation of the end effector (such as whether jaws are closed, open, or partially open), the state of power of a powered instrument (such as whether it is on or off), the state of activation of a sucker or irrigation instrument, the temperature of an instrument, and whether there are any vibrations, such as harmonic vibrations, of the instrument.

The visual processor is suitably configured to render the icon in dependence on additional information relating to the state of the instrument. Such additional information can comprise an indication of the rotational position of a joint in a rotational range of the joint. For example, a roll joint might have a ±360° rotational range (i.e. the joint can be rotated 720° between one limit of rotation and the other limit of rotation). Other rotational ranges are possible. It may not be apparent to a surgeon where within this range the instrument is from the rendering of the icon in the relevant image pose position. The visual processor is thus suitably configured to render the icon to include a range or scale showing the rotational range of the joint in or near the image of the end effector itself. The visual processor is suitably configured to render the icon to include a marker or indicator on the range or scale to show the rotational position of the instrument. The range or scale suitably matches the icon (or the remainder of the icon). Where the icon is provided in a circular icon area, for example by being provided on a circular background, the scale can comprise an arc. Similarly, where the icon is provided in an oval icon area, for example by being provided on an oval background, the scale can comprise an arc. Where the icon is provided in a square or rectangular icon area, for example by being provided on a square or rectangular background, the scale can comprise a line or bar.

The scale need not circumscribe the icon, but can be provided to one side of the icon. For example, where the icon is provided in a circular or oval icon area, the scale can comprise an arc akin to a fuel gauge, i.e. a relatively short arc. The curvature of the arc suitably corresponds to the curvature of the boundary of the icon area.

In the example above where a joint has a ±360° range, and the scale is an arc, the scale can represent −360° at one end of the arc (for example, the left end) and +360° at the other end of the arc (for example, the right end). The visual processor or the kinematics controller is suitably configured to calculate the rotational position of the instrument within the range, and to generate a marker on the scale to indicate the rotational position. I.e., where the instrument is at a rotational position that is +180° from a mid-point of the possible rotation, the visual processor is configured to generate the marker at a position along the arc that corresponds to +180°. In the example above, this would be halfway (for a linear axis) between a centre-point of the arc (representing the mid-point of the possible rotation between −360° and +360°) and the right end of the arc (representing +360°).

The icon is suitably rendered to show the determined image pose position on the display device 306 to enable identification of which of the possible available instruments 320 is the active instrument. In other words, if one of the instruments is pointing to the left (as viewed on the display device) and another instrument is pointing to the right, and the representation of the instrument is shown as pointing to the left, then the user can easily identify that the instrument pointing to the left is the one being controlled at that time.

Figure 5:
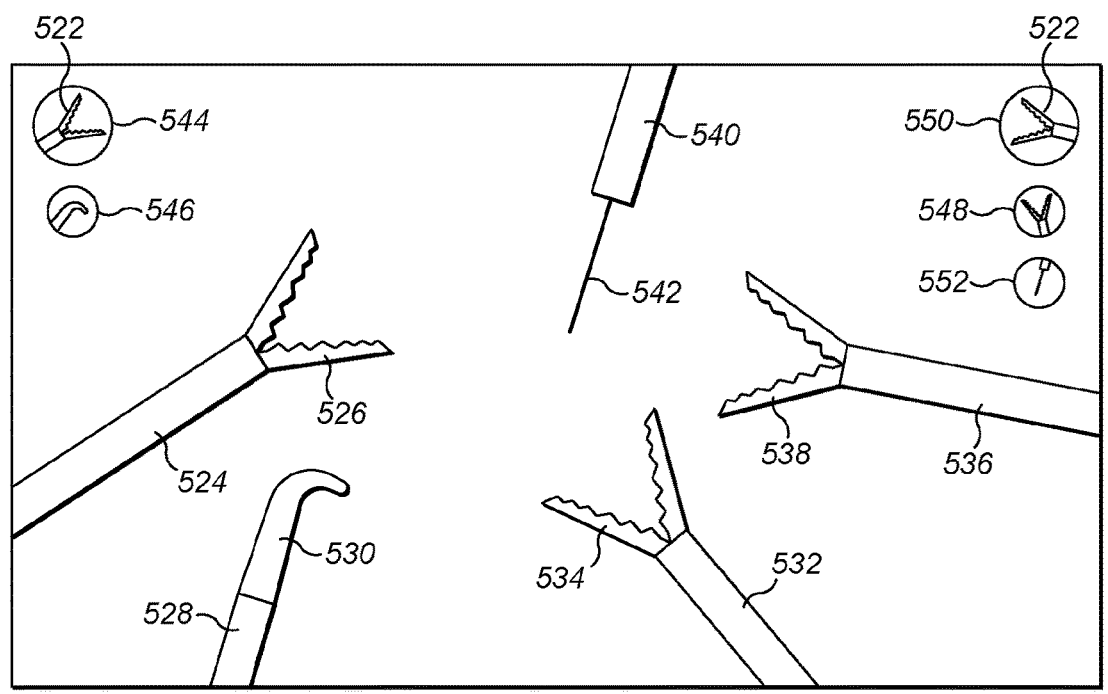
FIG. 5 schematically illustrates a representation of a display device showing an image.

An image displayed on a display device 306 is schematically represented in FIG. 5. The image shows distal portions of instruments comprising end effectors. The illustrated image includes a first instrument 524 (the distal portion of a shaft of the instrument is visible in the image) provided with a first end effector 526, a second instrument 528 provided with a second end effector 530, a third instrument 532 provided with a third end effector 534, a fourth instrument 536 provided with a fourth end effector 538 and a fifth instrument 540 provided with a fifth end effector 542. The image also includes representations (icons) of the first 544, second 546, third 548, fourth 550 and fifth 552 end effectors. In the example shown, the representation of the first end effector 544 and the representation of the fourth end effector 550 are shown larger than those of the other end effectors to indicate that these are the active end effectors 522. The representation of the first end effector 544 is shown on the left hand side of the display device to show that the first end effector 526 is being controlled by a first of the input devices, for example a left hand input device. The representation of the fourth end effector 550 is shown on the right hand side of the display device to show that the fourth end effector 538 is being controlled by a second of the input devices, for example a right hand input device.

Suitably, the location of each of the representations of the end effectors indicates which input device can be used to control that end effector. That is to say, the position of the representation of the second end effector 546 on the left hand side of the display device indicates that it can be controlled by the first input device. The position of the representations of the third 548 and fifth 552 end effectors on the right hand side of the display device indicate that they can be controlled by the second input device.

In some examples, any association between controllers (the input devices) and instruments is possible. In other words, the first input device can suitably couple to any instrument, and hence to any end effector. The first input device may be restricted from coupling to a particular instrument where that particular instrument is coupled to the second input device. Similarly, the second input device can suitably couple to any instrument. The second input device may be restricted from coupling to a particular instrument where that particular instrument is coupled to the first input device.

In the illustrated example, the representation of the active end effector is contained in a larger circle than those of the non-active end effectors. Use of other shapes or combinations of shapes is also possible. In this example the representation of the active end effector is shown at the top of the group of possible end effectors, i.e. the representation of the active end effector is shown above those of the non-active end effectors. This also serves to highlight to the user which of the end effectors is the current active end effector. However, providing the representations of the end effectors in, for example, circles, and causing the representation of the active end effector to be at the top of the group of possible end effectors is not necessary in all examples. Further, in some examples, combinations of these approaches are possible.

Suitably, the system is configured to highlight to the user which of the end effectors is the current active end effector by causing the corresponding representation of that end effector to change in at least one of size, position, position in a list of other representations, colour, lighting, background, outline, highlight image and visual effect such as a glow effect. Additionally or alternatively the system may be configured to highlight to the user the active end effector by causing the corresponding representation of that end effector to change from being two-dimensional to being three-dimensional, or from being three-dimensional to being two-dimensional.

For example, the representation can be larger for an active end effector than for a non-active end effector. The representation can be indented from the edge of the image (or closer to the edge of the image) for an active end effector compared to the position of a representation of a non-active end effector. The representation of an active end effector can be placed higher or lower in a list, such as a vertical list, or to the right or left in a list, such as a horizontal list, of possible end effectors, compared to one or more non-active end effectors. Preferably, as illustrated in FIG. 5, the list is a vertical list, and the active end effector representation is located at the top of the list. In this case the active end effector representation is thus located closest to the corner of the image. In other examples in which the list of representations of possible end effectors is located horizontally and/or towards the bottom of the image, the active end effector representation may similarly be provided closest to the corner of the image (or to another easily determinable feature). This can allow quick identification of the active end effector. In general, a display will comprise a working area of the display configured to display an image. Typically, a display will be rectangular, and the working area will also be rectangular, but this need not be the case. Suitably the icons will be arranged towards or at the right or left margins, and/or towards or at the upper or lower margins, of the working area of the display, so as to reduce or minimise the interference of the icons with the working area.

The representation of the active end effector can be provided in a different colour from the representations of the non-active end effectors, such as in a brighter and/or more distinct colour. In one example, representations of the non-active end effectors are provided in black and white and the representation of the active end effector is provided in full colour.

As described above, the visual processor is suitably configured to generate the icon so as to match the instrument, for example by matching a visual indication such as a pattern, orientation, profile and/or colour. In some examples, colours can be applied to the instruments, or at least portions of the instruments that will appear in the image captured by the imaging device, such as the end effector and/or the distal portion of the instrument shaft. The icons can be rendered to match these colours. Thus, a particular instrument shaft can be coloured green, and the icon on the display corresponding to that instrument can also be coloured green. This permits a quick and intuitive identification of the correspondence between the instrument and the icon. The colour can be chosen in dependence on the instrument type, for example all gripper instruments can be coloured green. Alternatively a series of colours can be chosen for each type of instrument. The colours chosen for one type of instrument are suitably different from the colours chosen for another type of instrument, though this need not be the case. For example, where an electrosurgical instrument is to be used together with two gripper instruments, the electrosurgical instrument may be coloured white, one gripper instrument may be coloured green and the other gripper instrument may be coloured blue. A desired colouring can be applied to the instruments by any suitable colour-application process, such as physical vapour deposition to colour stainless steel and anodising to colour aluminium.

The colour to apply to the icon in the display can be determined on the basis of data stored in a radio frequency identification (RFID) tag on the instrument. The central processor is suitably configured to query the data stored in the RFID tag. The stored data suitably comprises the colour corresponding to that instrument. Thus, the central processor can match the colour of the icon to that of the instrument in dependence on the stored data.

The instrument itself need not be coloured. The colour can be applied virtually, for example on the interface. Thus, the central processor is suitably configured to determine a colour to associate with the instrument, on the basis of data stored in an RFID tag on the instrument, or in any other suitable way, and to generate an overlay on or as part of the displayed image to colour the instrument. The whole of the instrument visible in the displayed image need not be virtually coloured. Suitably, to avoid obscuring the operation of the end effector, the end effector is not virtually coloured. Suitably the central processor is configured to apply colour to a more limited region associated with the instrument, for example an area such as a circular area on the instrument shaft, away from the end effector. More generally, the virtual colour can be applied to a flag associated with the instrument, which need not exactly align with the outline of the instrument viewed on the display. The generation of the overlay, or the application of the virtual colouring, is suitably handed by the visual processor.

The representation of the active end effector can be shown as a three-dimensional representation, whilst the representations of the non-active end effectors are preferably shown as two-dimensional representations. This can be particularly effective when the image is displayed in three-dimensions, as this can permit the user to more naturally see the correspondence between the representation for the active end effector and the respective end effector as visualised in the image.

Figure 6A:
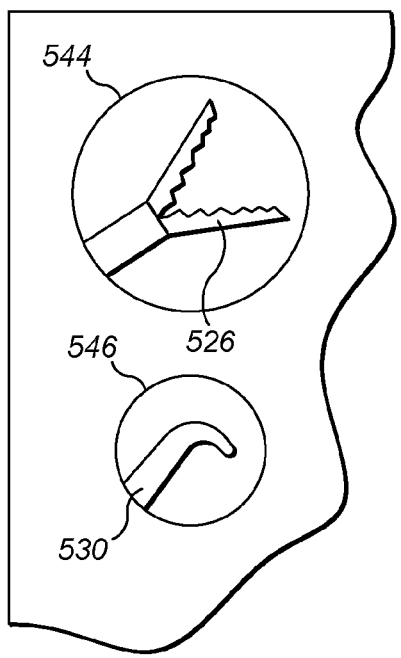
FIG. 6a shows an enlargement of the top left portion of FIG. 5.

Referring now to FIG. 6a, which shows an enlargement of the upper left portion of the image shown in FIG. 5, the representation of the active end effector 544 for the first input device is shown to be a representation of the first end effector 526. The representation of the first end effector is in the same pose position as the first end effector 526 itself (as can be seen from a comparison between FIGS. 5 and 6a). The representation of the non-active end effector 546 is shown to be a representation of the second end effector 530. The representation of the second end effector is in the same pose position as the second end effector 530 itself.

Figure 6B:
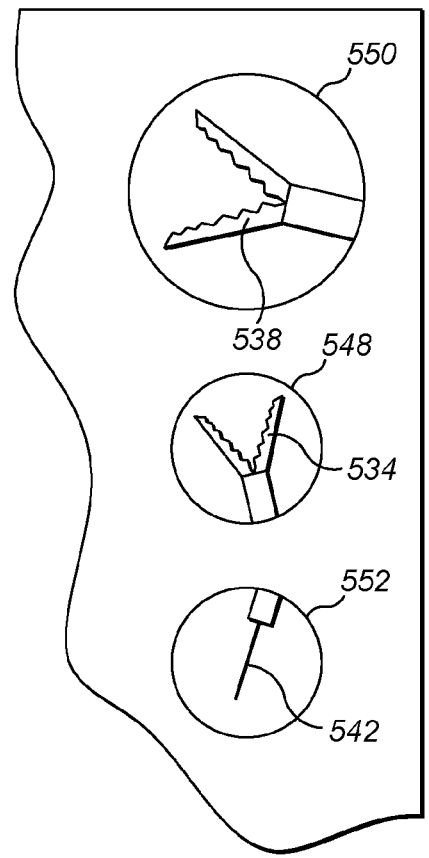
FIG. 6b shows an enlargement of the top right portion of FIG. 5.

Referring now to FIG. 6b, which shows an enlargement of the upper right portion of the image shown in FIG. 5, the representation of the active end effector 550 for the second input device is shown to be a representation of the fourth end effector 538. The representation of the fourth end effector is in the same pose position as the fourth end effector 538 itself (as can be seen from a comparison between FIGS. 5 and 6b). The representations of the non-active end effector 548, 552 are shown to be representations of the third end effector 534 and the fifth end effector 542. The representations of the third and fifth end effectors are in the same pose positions as the respective end effectors 534, 542 themselves.

In some examples, the representations of the non-active end effectors need not be in the same pose positions as the respective end effectors.

Referring again to FIG. 6b, it can be seen that whilst there are three possible end effectors in the illustrated example which can be operatively associated with the second input device: a needle-like end effector 542 and two gripper-type end effectors 534, 538, the fourth end effector 538 (one of the gripper-type end effectors) can be identified as being the active end effector from a quick comparison of the icon for the active end effector (the representation of the active end effector 550) with the image shown on the display device.

Thus the present approach avoids the need for end effectors to be moved to find out which of the end effectors is the active end effector. This can therefore avoid unnecessary movement, and reduce potential tissue damage.

Figure 7:
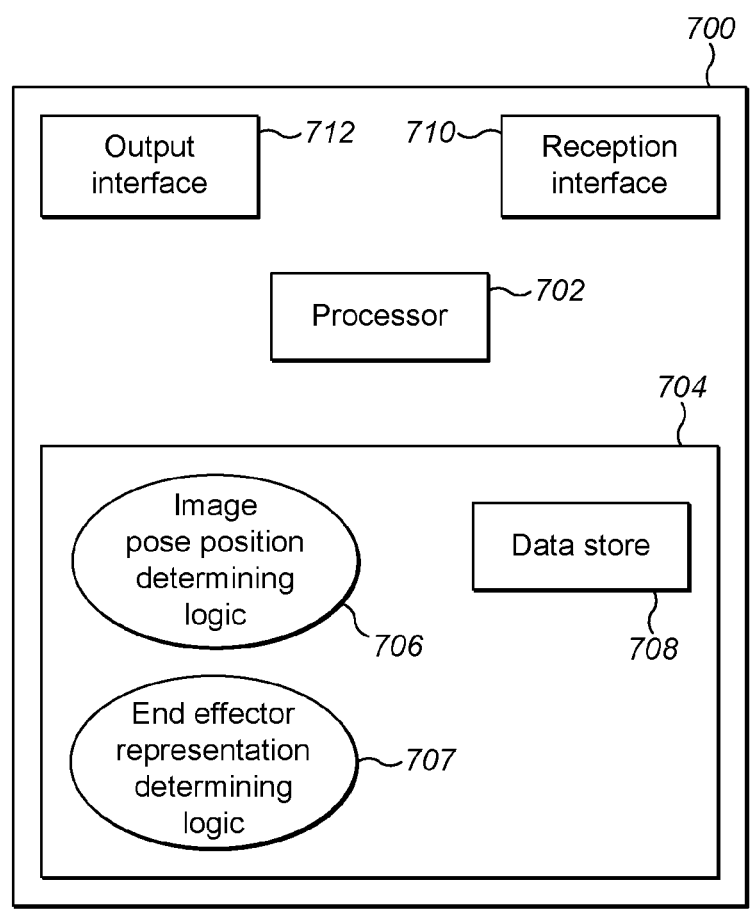
FIG. 7 schematically illustrates a computing-based device.

Reference is now made to FIG. 7. FIG. 7 illustrates a computing-based device 700 in which the robotic surgical system 300 can be implemented. The computing-based device may be an electronic device. The computing-based device illustrates functionality for receiving joint state signals and/or instrument state signals, storing joint state signals and/or instrument state signals, determining a pose position of an instrument and an imaging device, computing an image pose position of the instrument, determining a representation of an end effector for display and outputting the representation of the end effector for display.

Computing-based device 700 comprises a processor 702 for processing computer executable instructions configured to control the operation of the device in order to perform the methods described herein. The computer executable instructions can be provided using any computer-readable media such as memory 704. Further software that can be provided at the computer-based device 700 includes image pose position determining logic 706 which is able to determine the image pose position of an instrument based, for example on the pose position of the instrument, as described above, and end effector representation (i.e. icon) determining logic 707. Alternatively, the image pose position determining logic 706 and/or the end effector representation determining logic 707 is implemented partially or wholly in hardware. A data store 707 may store data such as joint state signals, instrument state signals and/or data relating to a previous state of the robot arm and instrument. Computing-based device 700 further comprises a reception interface 710 which receives the joint state signals, the instrument state signals and/or the data relating to the previous state of the robot arm and instrument. Computing-based device 700 further comprises an output interface 712 which outputs the determined representation of the end effector to the display device for display. FIG. 7 illustrates a single computing-based device in which the robotic surgical system 300 is implemented. However, the functionality of the robotic surgical system 300 may be implemented on separate computing-based devices.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic system for determining an operative state of an instrument of a plurality of instruments controllable by an input device, the input device being operatively coupleable to one instrument of the plurality of instruments at a time, the surgical robotic system comprising a processor configured to:
   obtain a state signal associated with an imaging device;
   for each of the plurality of instruments:
      obtain a state signal associated with the instrument;
      determine an image pose position of the instrument in dependence on the obtained state signal associated with the instrument and the obtained state signal associated with the imaging device;
      determine an icon for display in dependence on the determined image pose position, the icon having a shape corresponding to the instrument and an orientation of the instrument; and
      output a display signal to cause a display device to display the icon, whereby the operative state of the instrument can be determined from the displayed icon;
   wherein each of the respectively displayed icons for each of the plurality of instruments is selectable by a user to operatively couple a corresponding instrument of the plurality of instruments to the input device.

2. A surgical robotic system as claimed in claim 1, in which the respective state signal associated with the respective instrument comprises at least one of a joint state signal associated with the respective instrument and an instrument state signal.

3. A surgical robotic system as claimed claim 2, in which the processor is configured to:
   receive at least one of the joint state signal associated with the respective instrument and the respective instrument state signal; and/or
   determine at least one of the joint state signal associated with the respective instrument and the respective instrument state signal in dependence on one or more instrument control signal transmitted by the processor.

4. A surgical robotic system as claimed in claim 2, in which at least one of the joint state signal associated with the respective instrument and the joint state signal associated with the imaging device comprises one or more of a position sensor signal and a torque sensor signal.

5. A surgical robotic system as claimed in claim 1, in which the state signal associated with the imaging device comprises at least one of a joint state signal associated with the imaging device and an imaging device state signal.

6. A surgical robotic system as claimed in claim 5, in which the processor is configured to;
   receive at least one of the joint state signal associated with the imaging device and the imaging device state signal; and/or
   determine at least one of the joint state signal associated with the imaging device and the imaging device state signal in dependence on one or more imaging device control signal transmitted by the processor.

7. A surgical robotic system as claimed in claim 1, in which the processor is configured to:
   determine a pose position of the respective instrument in dependence on the state signal associated with the respective instrument;
   determine a pose position of the imaging device in dependence on the state signal associated with the imaging device; and
   determine the respective image pose position in dependence on the pose position of the respective instrument and the pose position of the imaging device.

8. A surgical robotic system as claimed in claim 7, in which the processor is configured to determine a coordinate transform in dependence on the determined pose position of the respective instrument and the determined pose position of the imaging device.

9. A surgical robotic system as claimed in claim 8, in which the processor is configured to determine a change in the pose position of at least one of the respective instrument and the imaging device, and to determine an updated coordinate transform in dependence on the determined change.

10. A surgical robotic system as claimed in claim 1, comprising a first instrument configured to output one of the respective instrument state signals, in which the one of the respective instrument state signals comprises a signal indicative of an arrangement of an end effector of the first instrument.

11. A surgical robotic system as claimed in claim 1, in which the processor comprises a kinematics controller, and the kinematics controller is configured to determine an interface state in dependence on the state signals, the interface state comprising data associated with the respective icon for display.

12. A surgical robotic system as claimed in claim 11, comprising a visual processor, the visual processor being configured to receive the interface state from the kinematics controller and to render the respective icon for display.

13. A surgical robotic system as claimed in claim 12, in which the kinematics controller is operable at a higher frequency than the visual processor.

14. A surgical robotic system as claimed in claim 1, in which the respective icon comprises a scale showing a rotational range of a joint, and the processor is configured to determine the rotational position of the joint and to cause the display on the scale of a marker indicative of the determined rotational position.

15. A surgical robotic system as claimed in claim 1, in which the shape of the respective icon matches that of:
   at least a portion of the respective instrument, and/or
   at least a portion of an end effector of the respective instrument.

16. A surgical robotic system as claimed in claim 1, in which a projection of the respective icon is away from an axis of the imaging device.

17. A surgical robotic system as claimed in claim 1, in which the processor is further configured to:
   obtain a further state signal associated with a further instrument;
   determine a further image pose position of the further instrument in dependence on the obtained state signal associated with the further instrument and the obtained state signal associated with the imaging device; and
   determine a further icon for display in dependence on the determined further image pose position, the further icon having a shape corresponding to the further instrument, and an icon pose position different from a pose position of the further instrument.

18. A surgical robotic system as claimed in claim 1, in which the shape of the respective icon is determined based on the operative state of the respective instrument.

19. A method of determining an icon for display in a robotic surgical system for determining an operative state of an instrument of a plurality of instruments controllable by an input device, the input device being operatively coupleable to one instrument of the plurality of instruments at a time, the method comprising:
   obtaining a state signal associated with an imaging device;
   for each of the plurality of instruments:
      obtaining a state signal associated with the instrument;
      determining an image pose position of the instrument in dependence on the obtained state signal associated with the instrument and the obtained state signal associated with the imaging device;
      determining an icon for display in dependence on the determined image pose position, the icon having a shape corresponding to the instrument and an orientation of the instrument; and
      outputting a display signal to cause a display device to display the icon, whereby the operative state of the instrument can be determined from the displayed icon;
   wherein each of the respectively displayed icons for each of the plurality of instruments is selectable by a user to operatively couple a corresponding instrument of the plurality of instruments to the input device.

* * * * *